US011648145B2

(12) United States Patent
Richardson et al.

(10) Patent No.: US 11,648,145 B2
(45) Date of Patent: May 16, 2023

(54) REMOVABLE LIGATURE RESISTANT RESTRAINT RING RECEPTACLE

(71) Applicants: Jed C. Richardson, Batavia, IL (US); Abdullah Shahzad, Aurora, IL (US)

(72) Inventors: Jed C. Richardson, Batavia, IL (US); Abdullah Shahzad, Aurora, IL (US)

(73) Assignee: Norix Group, Inc., West Chicago, IL (US)

( * ) Notice: Subject to any disclaimer, the term of this patent is extended or adjusted under 35 U.S.C. 154(b) by 1097 days.

(21) Appl. No.: 16/237,522

(22) Filed: Dec. 31, 2018

(65) Prior Publication Data

US 2020/0206014 A1    Jul. 2, 2020

(51) Int. Cl.
*A61F 5/37*     (2006.01)
*E05B 73/00*    (2006.01)
*A47B 97/00*    (2006.01)

(52) U.S. Cl.
CPC ............ *A61F 5/3776* (2013.01); *A47B 97/00* (2013.01); *A61F 5/3761* (2013.01); *A61F 5/3769* (2013.01); *E05B 73/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,480,662 A * | 8/1949 | McKinzie | ............... | F41C 23/02 24/607 |
| 3,897,778 A * | 8/1975 | Forbes-Robinson | ........................ | A61F 5/3784 5/83.1 |
| 4,074,373 A * | 2/1978 | Garofalo | .................. | A61B 6/04 378/204 |
| 4,789,183 A * | 12/1988 | Wolfer | .................... | B60R 21/12 280/801.1 |
| 4,807,864 A * | 2/1989 | Young | .................... | A61G 13/12 5/617 |
| 4,998,308 A * | 3/1991 | Farago | .................. | A61F 5/3776 5/503.1 |
| 5,038,799 A * | 8/1991 | Fowler | .................. | A61F 5/3761 128/878 |
| 5,546,962 A * | 8/1996 | Power | .................. | A61F 5/3761 128/869 |
| 6,152,645 A * | 11/2000 | Sanford | ................ | F16D 41/064 403/322.2 |
| 7,562,481 B2 * | 7/2009 | Esch | ....................... | F41C 23/02 24/2.5 |
| 7,654,027 B1 * | 2/2010 | Grover | .................. | F16B 21/165 403/322.2 |

(Continued)

*Primary Examiner* — Monica E Millner
(74) *Attorney, Agent, or Firm* — Applied Patent Services, PC; James D Palmatier

(57) ABSTRACT

The removable restraint ring receptacle comprises a base for attachment to a furniture piece. The base adapted to receive a ligature resistant fastener. A restraint ring engaged by the fastener. The ligature resistant fastener may be a ball pin lock having a conical or rounded head. The head bearing against the restraint ring. The ligature resistant fastener further comprising a collar adapted to extend from the head to the base. The collar comprising a tapered outside surface adapted to span the gap between the head and the base when the ring is removed thereby providing a tapered protrusion to prevent the attachment of a ligature or snagging of clothes.

15 Claims, 11 Drawing Sheets

(56) References Cited

U.S. PATENT DOCUMENTS

| | | | |
|---|---|---|---|
| 8,500,358 B1* | 8/2013 | Cassidy | A63B 23/0355 |
| | | | 403/322.2 |
| 8,516,732 B2* | 8/2013 | Burnsed, Jr. | F41C 33/002 |
| | | | 403/322.2 |
| 9,248,537 B2* | 2/2016 | O'Neill | F16B 13/04 |
| 10,550,609 B2* | 2/2020 | Llewellyn | B63B 25/28 |
| 10,980,660 B2* | 4/2021 | Richardson | A61F 5/3792 |
| 2008/0077151 A1* | 3/2008 | Kring | A61B 17/132 |
| | | | 606/88 |
| 2010/0062634 A1* | 3/2010 | Hardy | H01R 13/74 |
| | | | 439/359 |
| 2017/0165097 A1* | 6/2017 | Patmore | A61F 5/3769 |
| 2018/0087867 A1* | 3/2018 | Tower | F41C 23/02 |
| 2019/0374371 A1* | 12/2019 | Richardson | E05B 73/00 |

* cited by examiner

FIG. 1
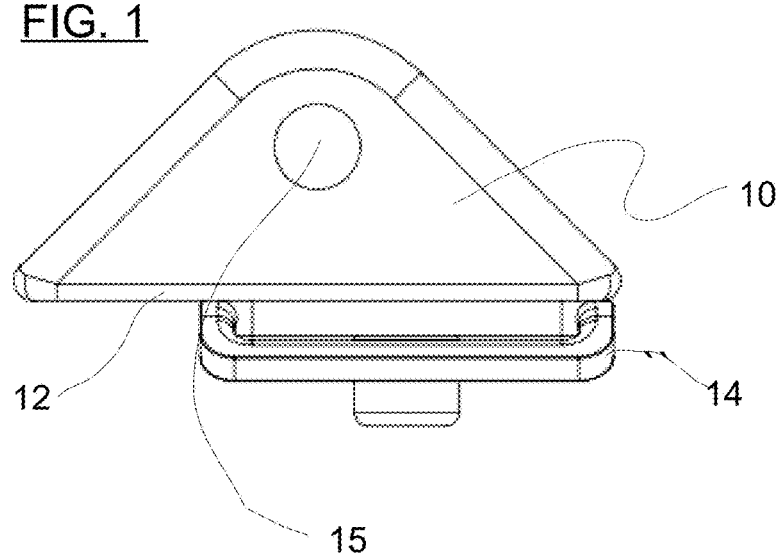
FIG. 2
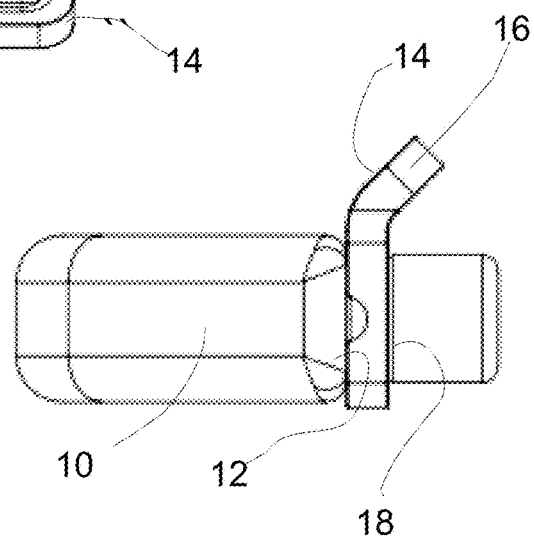
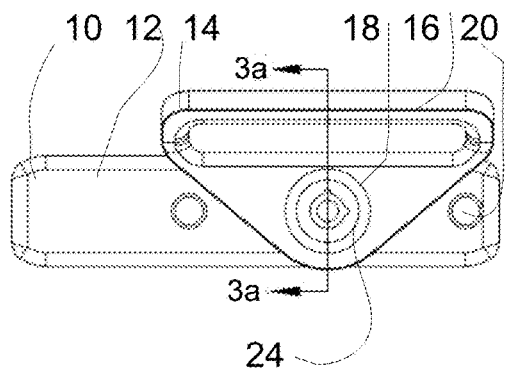
FIG. 3
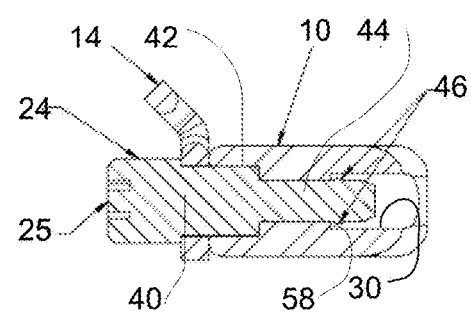
FIG. 3a

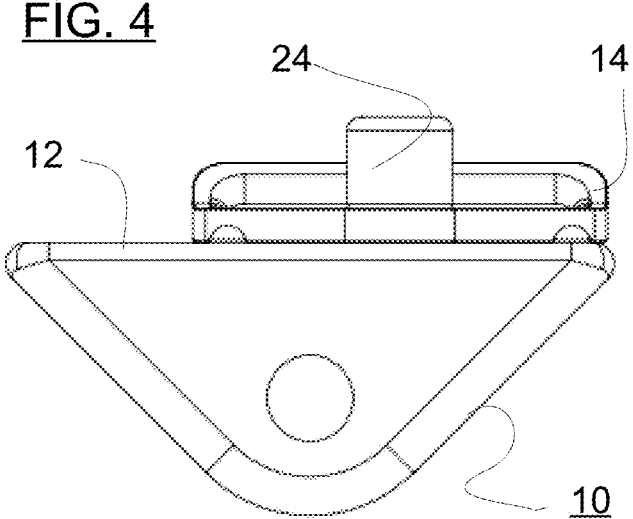
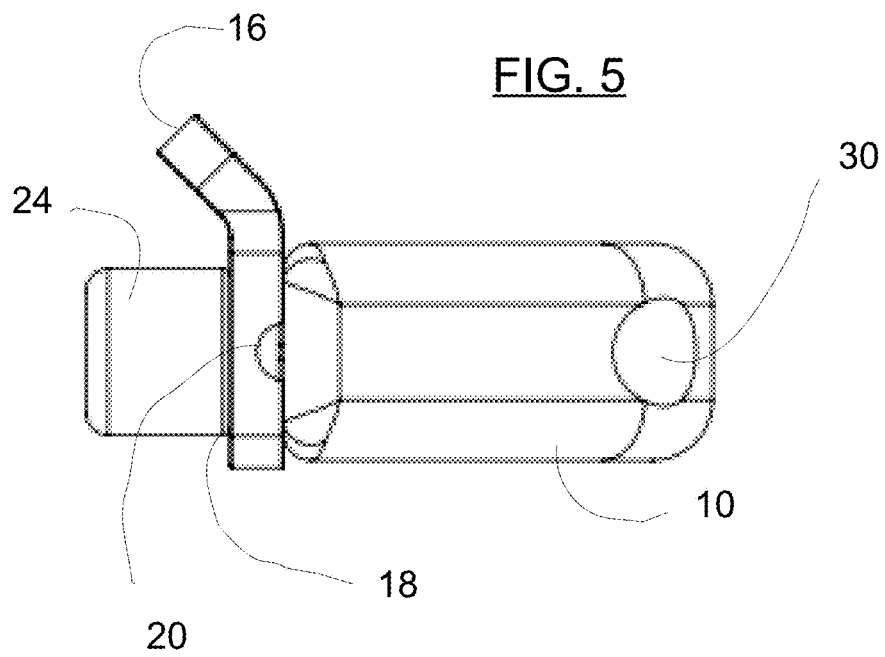

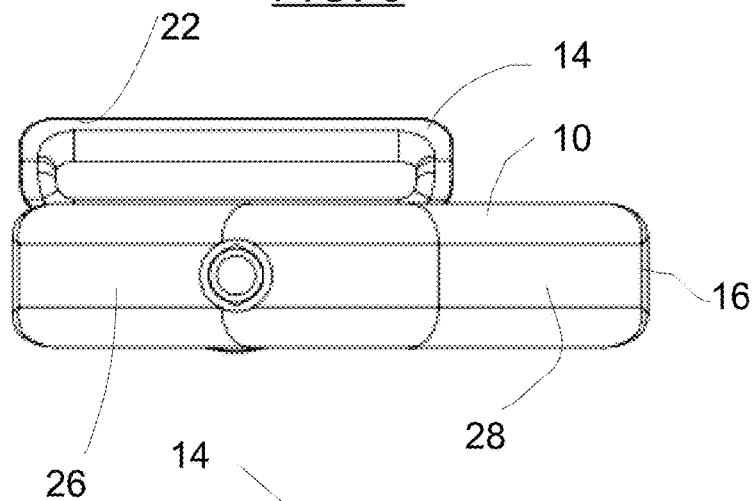
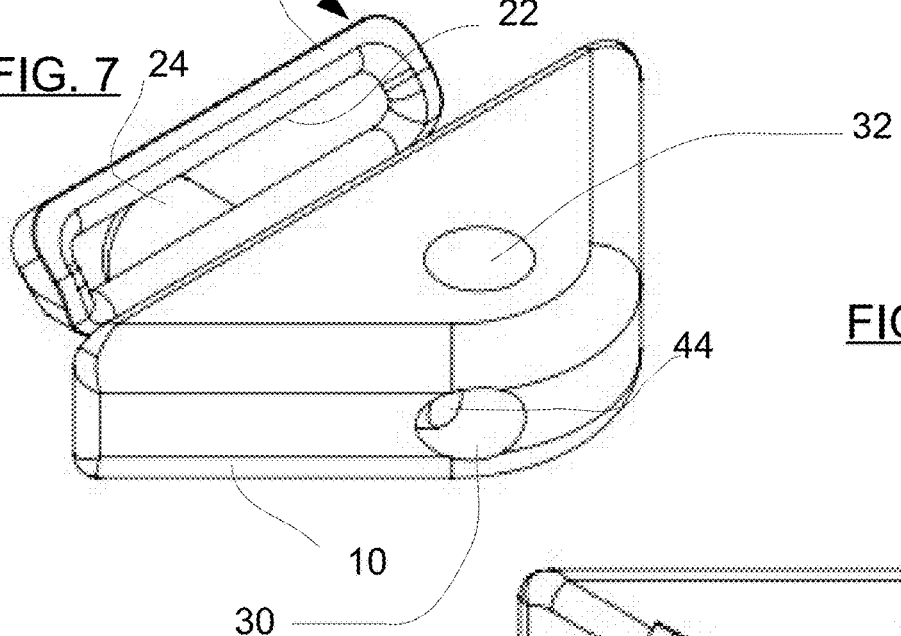
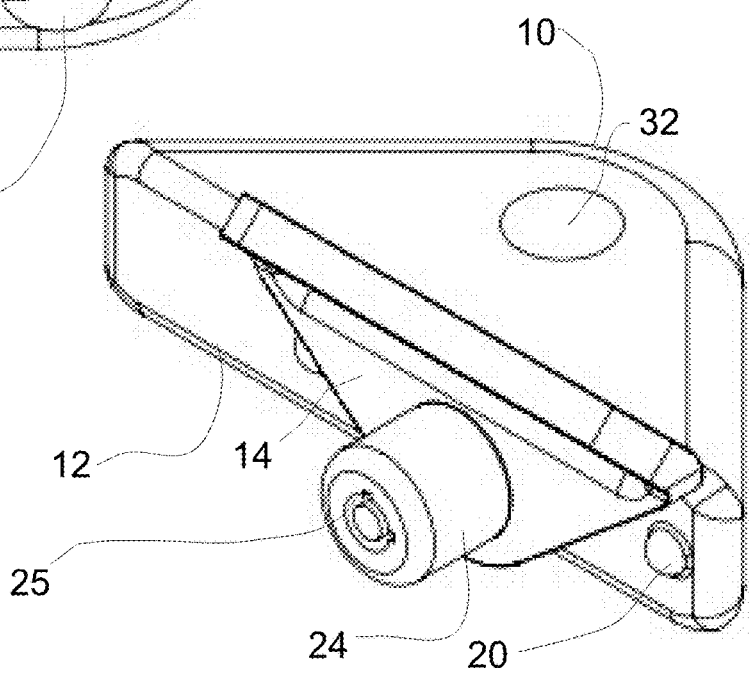

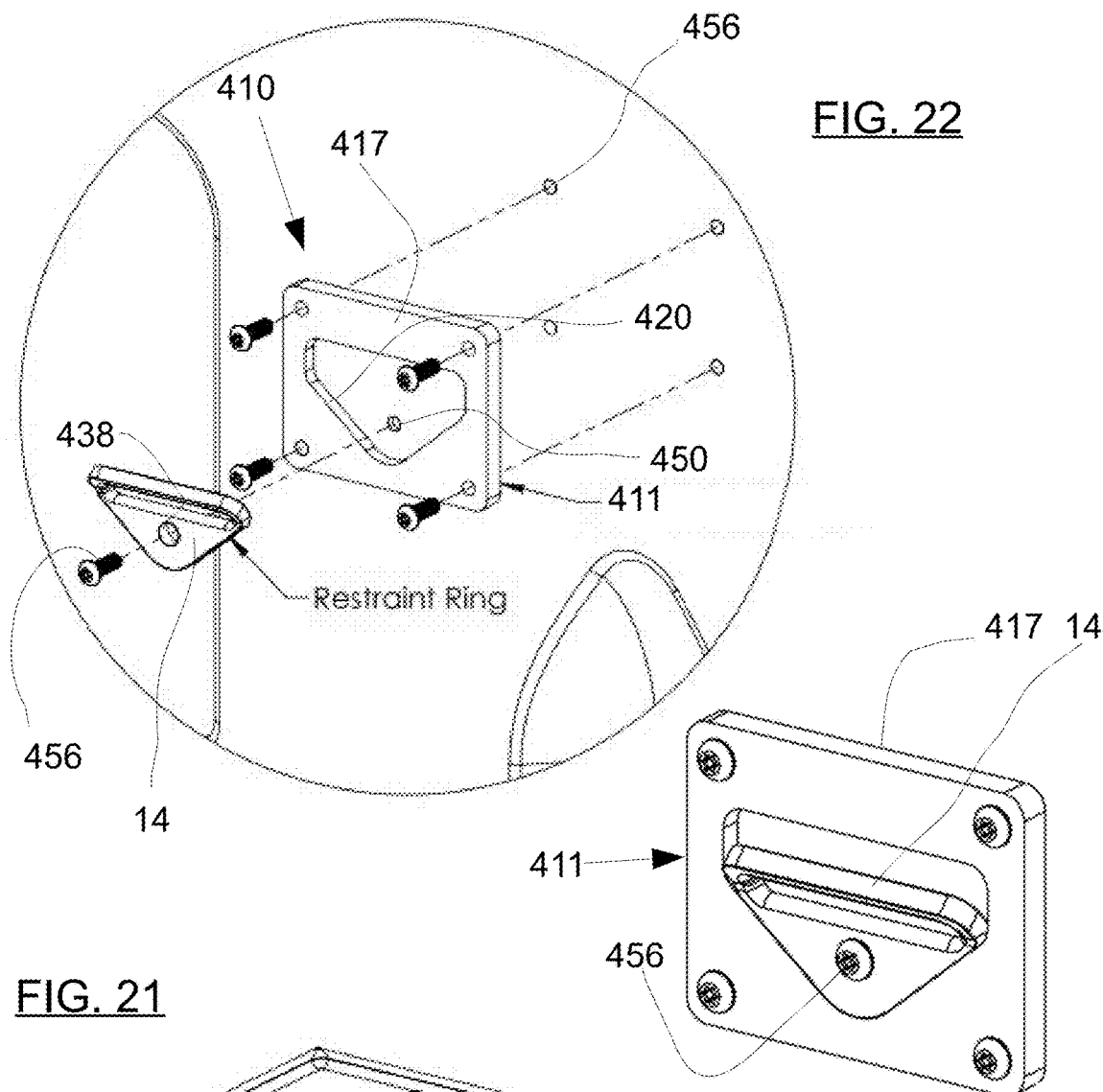
FIG. 22
FIG. 23
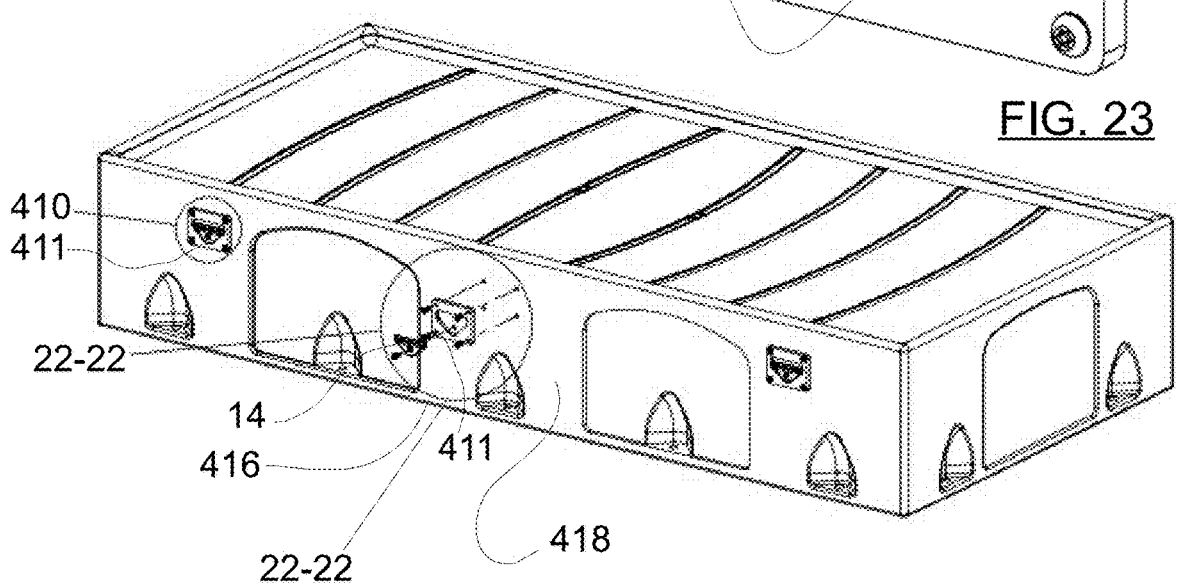
FIG. 21

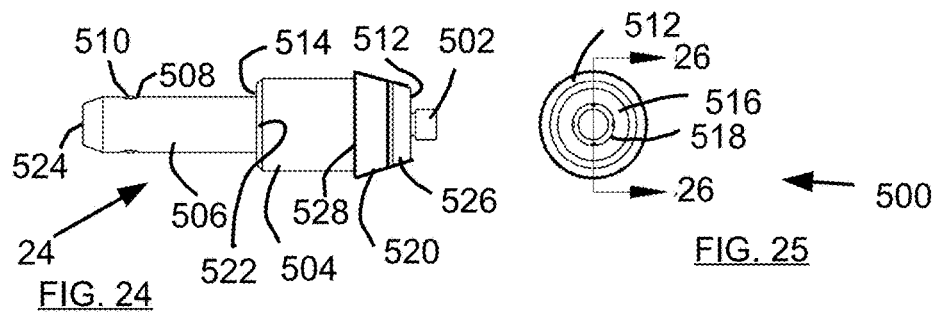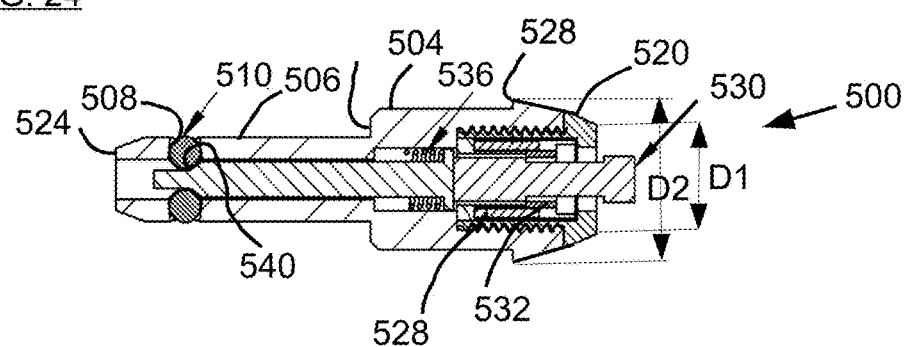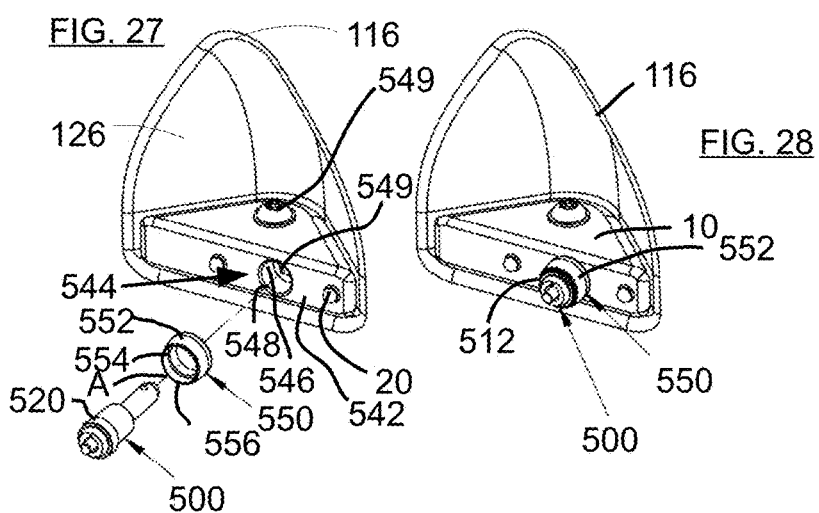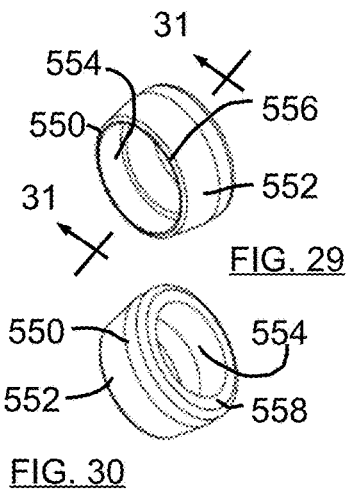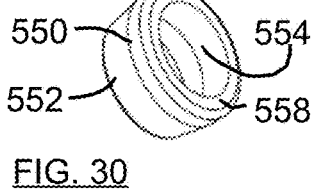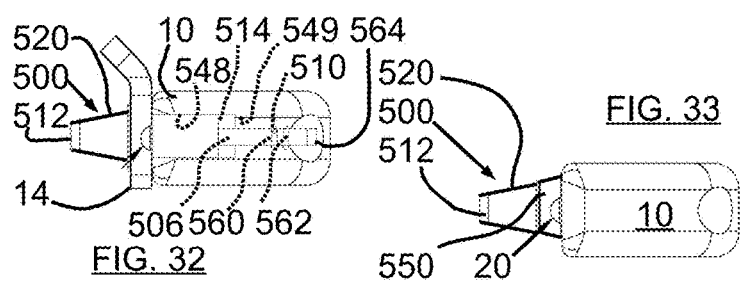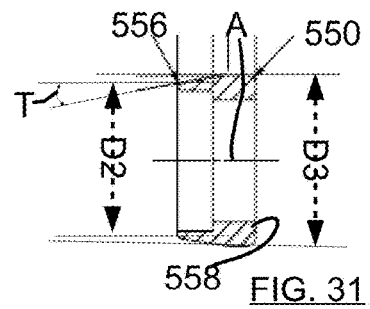

REMOVABLE LIGATURE RESISTANT RESTRAINT RING RECEPTACLE

FIELD OF THE INVENTION

The present invention relates to intensive use furniture specifically a removable low profile restraint ring receptacle having a ligature resistant profile.

BACKGROUND OF THE INVENTION

The present invention relates to a removable low profile restraint ring receptacle having a ligature resistant outer surface. Restraint rings are known in the prior art as a ring, usually of metal, attached to a piece of furniture such as a bed or chair. The restraint ring is used as an anchor to secure a subject to the furniture using straps or hand cuffs for the safety of the subject and the attendees working with the subject. The prior art teaches bolting or otherwise securely attaching the restraint ring to the furniture. Generally, furniture is designed having a restraint ring mounted in a predetermined location relative to the subject's position on the furniture.

The need for a restraint ring may arise based on subjects in the facility. Furniture designed without a restraint ring may need to be adapted to utilize a restraint ring. In some facilities, the restraint ring may only be occasionally used based on a particular subject's need. The removable ligature resistant restraint ring receptacle may adapt such furniture to utilize a restraint ring by a mount attachable to the furniture. The mount adapted to attach to the furniture. The mount adapted to receive a restraint ring thereon for periodic use.

Furthermore, some facilities may desire to remove such restraint ring from furniture when not in use to project an image of restraint free treatment. When the restraint ring is not needed, it may present an undesirable image of the furniture or the facility. However, when the restraint ring is needed, the need may arise quickly and the restraint ring may need to be quickly attached to the furniture.

Prior art attachment of restraint ring teaches permanent or difficult to remove attachments of restraint rings to furniture, Such attachments may be designed for safety as well as security. The safety of a subject needing to be restrained includes preventing danger of harm by ligature. Such harm may facilitated by the provision of a ligature tie off whereby the subject may cause personal harm. Prior art attachments teach the use of non removable low profile fasteners or attachment by welding or adhesion methods known in the art.

It is an object of the removable low profile restraint ring receptacle to provide a mount adapted to quickly attach securely to furniture. The mount may be adapted to receive a low profile or tapered fastener attaching a restraint ring to the mount.

It is a further object of the removable low profile restraint ring receptacle to provide a fastener adapted to quickly attach a restraint ring to the mount.

It is another object of the removable low profile restraint ring receptacle to provide a fastener having a ligature resistant profile when securing the restraint ring to the mount to prevent ligature harm.

It is another object of the removable low profile restraint ring receptacle to provide a fastener having a ligature resistant tapered profile when the restraint ring is removed from the mount to prevent ligature harm Accordingly, it is desirable to provide a removable low profile restraint ring receptacle having a mount adapted to attach to furniture and further adapted to removably receive a restraint ring by a fastener that quickly locks the restraint ring to the mount, the fastener having a tapered shape to prevent ligature harm. The fastener having a tamper resistant release to quickly remove the restraint ring from the mount, the fastener adapted to maintain the tapered shape extending from the mount.

SUMMARY OF THE INVENTION

The present invention may comprise a removable low profile restraint ring receptacle having a base adapted to attach to a furniture piece such as a bed or chair. The base having a furniture surface on the furniture and a ring surface. The base may be attached to the furniture by a low profile, tamper resistant bolt extending through a bolt hole in the mount. The bolt hole extending from the furniture side to the ring side. The ring side having a pin cavity and a alignment nub. The pin cavity having an opening in the ring side in fluid communication with a stepped interior surface defining a body chamber and a lock chamber. The lock chamber may have a ball recess or groove formed as a channel in the wall concentric with the lock chamber.

The fastener may be a ball lock pin such as a modified PLK6-1500 as provided by Pivot Point of Hustisford, Wis., engineers comprising a custom ball lock pin. The fastener may comprise a head, a body and a lock tube. The head having a tapered, conical or rounded, low-profile shape. The head shape is tapered to prevent the attachment of ligatures. The body may be between the head and the lock tube, the lock tube extending from the body. When in the pin cavity, the head may protrude from the mount, the body is in the body chamber and the lock tube in the lock chamber. A ball in the lock tube may protrude from the lock tube. The ball in the ball recess. A cam extending from the head bearing against the ball to retain the fastener in the pin chamber by the ball in the ball recess.

The fastener may be adapted to lock the ball lock in place by urging the ball to protrude from the lock tube by a push to lock push button in the head. A key-unlocking mechanism in the fastener may be adapted to unlock the push-button actuator and allow the ball to retract into the lock tube and out of the ball recess thus releasing the fastener from the mount. The low profile, specially shaped tapered head is adapted to prevent ligature tie offs or snagging the restraints, clothing or other materials that may cause harm.

The removable low profile restraint ring receptacle is further adapted resist ligature or snagging by a collar disposed on the body, the collar extending from the head to provide a continuation of the tapered profile when the ring is not attached to the mount. The ring may be removed and the fastener replaced in the mount. A gap between the ring side and the head is concealed by the collar concentrically mounted on the body between the head and the ring side of the mount.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE SEVERAL VIEWS OF THE DRAWING

FIG. 1 is a top plan view of a first embodiment of the present invention.

FIG. 2 is a right side elevation view of the first embodiment of the present invention of FIG. 1

FIG. 3 is a front elevation view of the first embodiment of the present invention of FIG. 1.

FIG. 3a is a section view of the first embodiment taken at approximately 3a-3a of FIG. 3.

FIG. 4 is a bottom plan view of the first embodiment of the present invention of FIG. 1.

FIG. 5 is a left plan view of the first embodiment of the present invention of FIG. 1.

FIG. 6 is a back elevation view of the first embodiment of the present invention of FIG. 1.

FIG. 7 is a top back perspective view of the first embodiment of the present invention of FIG. 1

FIG. 8. is a top front perspective view of the first embodiment of the present invention of FIG. 1.

FIG. 21 is an perspective exploded view of a fifth embodiment of the present invention.

FIG. 22 is an exploded section view of the fifth embodiment of the present invention taken at approximately 22-22 of FIG. 21.

FIG. 23 is a section view of the fifth embodiment of the present invention taken at approximately 22-22 of FIG. 21.

FIG. 24 is a side elevation view of an alternate ball lock pin.

FIG. 25 is an end elevation view of a ball lock pin of FIG. 24.

FIG. 26 is an section view of a ball lock pin of FIG. 24 taken at approximately 26-26 of FIG. 25.

FIG. 27 is a perspective exploded view of ball lock pin of FIG. 24 and a collar adapted to engage the ring base.

FIG. 28 is a perspective view of ball lock pin and collar of FIG. 27 attached to the ring base.

FIG. 29 is a front perspective view of the collar of FIG. 27.

FIG. 30 is a rear perspective view of the collar of FIG. 27.

FIG. 31 is a section view of the collar of FIG. 29 taken at approximately 31-31.

FIG. 32 is a side elevation view of the ball lock pin of of FIG. 24 attaching the base to the ring FIG. 33 is a side elevation view of the ball lock pin of FIG. 24 and collar of FIG. 29 attached the base

DETAILED DESCRIPTION OF THE INVENTION

Figure 9:
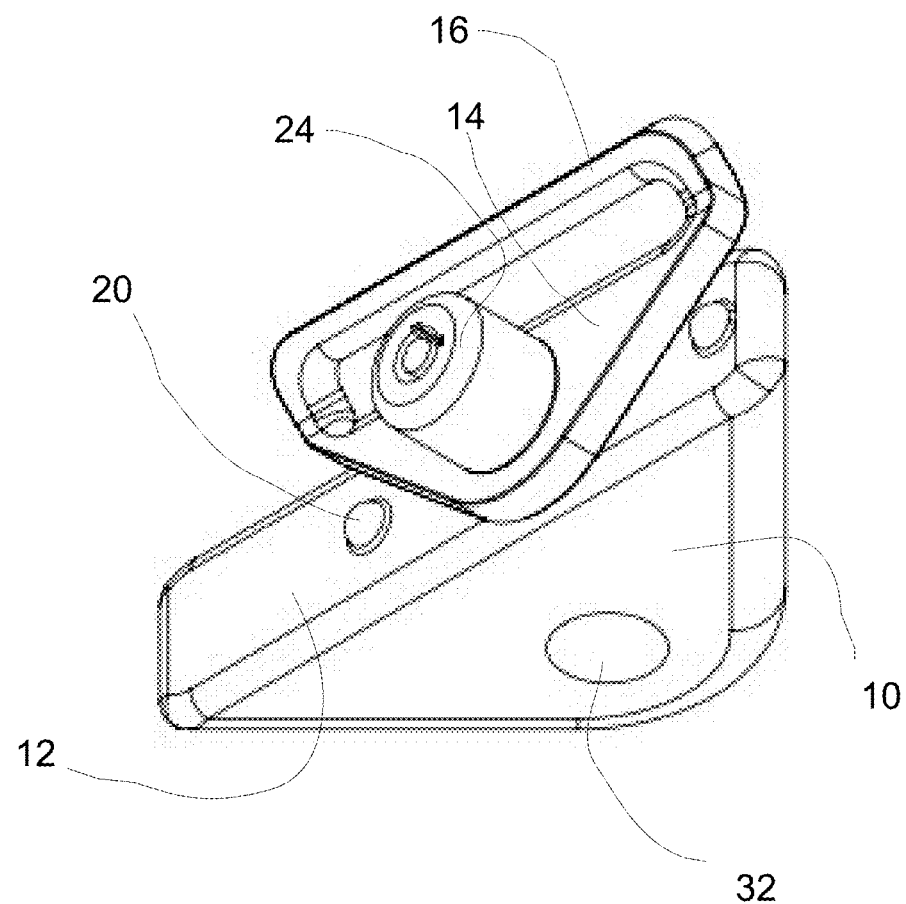
FIG. 9 is a bottom front perspective view of the first embodiment of the present invention of FIG. 1.
Figure 10:
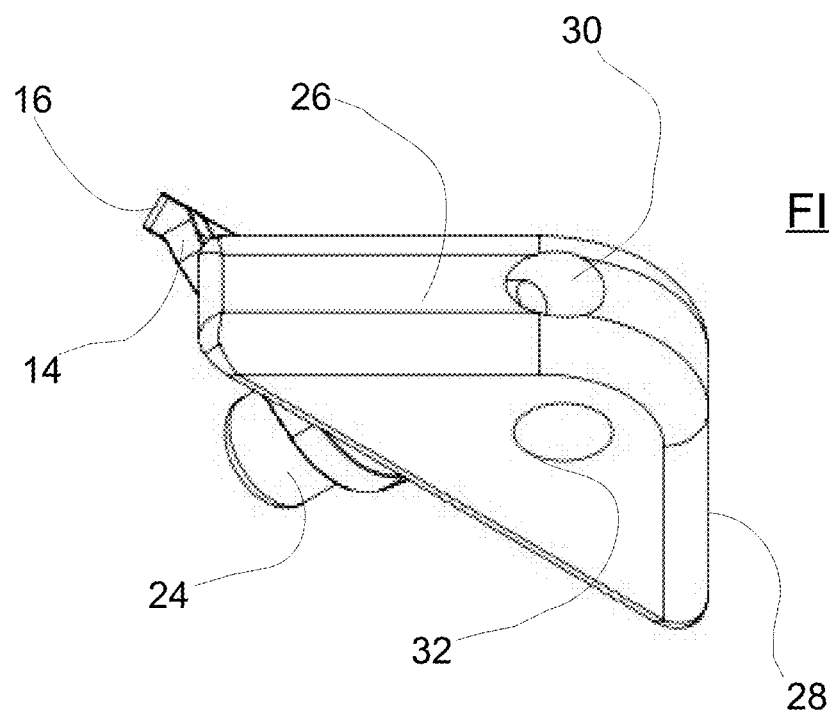
FIG. 10 is a bottom perspective view of the first embodiment of the present invention of FIG. 1.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention. It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting. It should be appreciated that the invention can be used for any suitable.

Referring to FIGS. 1-5 the invention comprises a base 10 having a mounting surface 12 and a restraint ring 14 attached to the mounting surface 12. The restraint ring 14 has an open loop portion 16 and a ring base 18. Mounting hole 15 extends through base 10. Quick release fastener 24 extends through ring base 18 in quick release hole 30. Quick release fastener 24 engages base 10 to secure restraint ring 14 to base 10. Stabilizers 20 on mounting surface 12 to urge restraint ring 14 to maintain a predetermined orientation with respect to base 10. It is preferable that open loop portion 16 is spaced from base 10. Quick release fastener 24 comprises head 40 bearing against restraint ring 14 to attach restraint ring 14 to base 10 having ring shaft extending through ring 14 and into base 10 with quick release shaft extending on quick release hole 30 to dispose locking mechanism 46 in position to bear against locking shoulder 58.

Referring to FIGS. 6-10, base 10 has a first side 26 and second side 28. Quick release hole 30 opens to first side 26 having quick release shaft 44 removably attached therein. Restraint ring 14 comprises strap opening 22 on open loop portion 16. Secure hole 32 extends through base 10 generally perpendicular to quick release hole 30. Quick release fastener 24 may have a release mechanism 25 adapted to securely release and prevent unauthorized removal of restraint ring 14.

Figure 11:
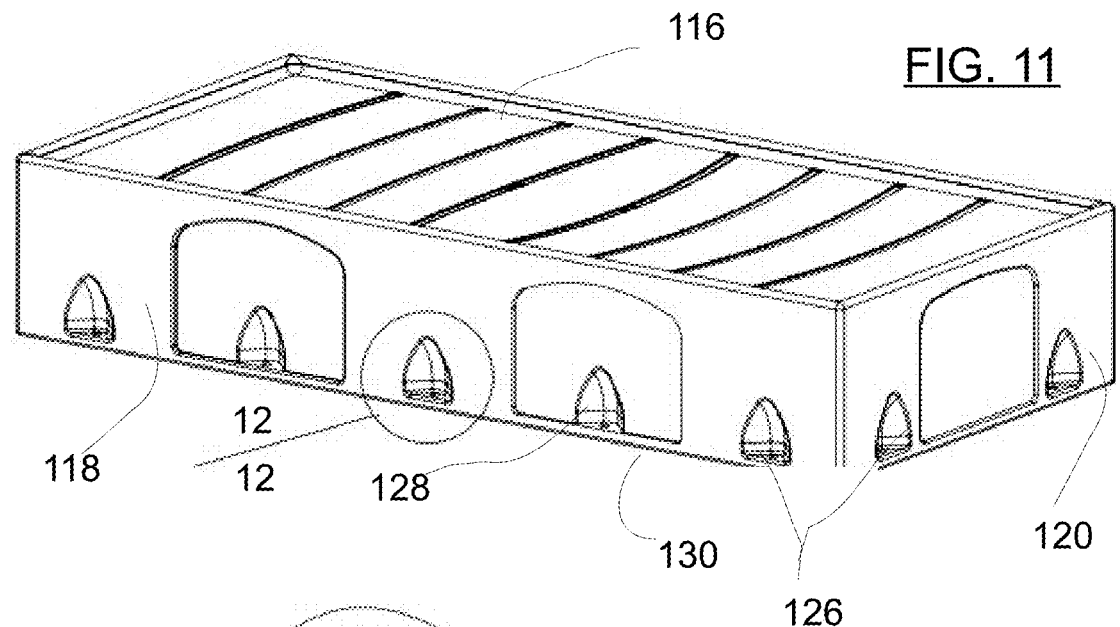
FIG. 11 is a perspective view of a bed adapted to attach to the first embodiment of the present invention of FIG. 1.
Figure 12:
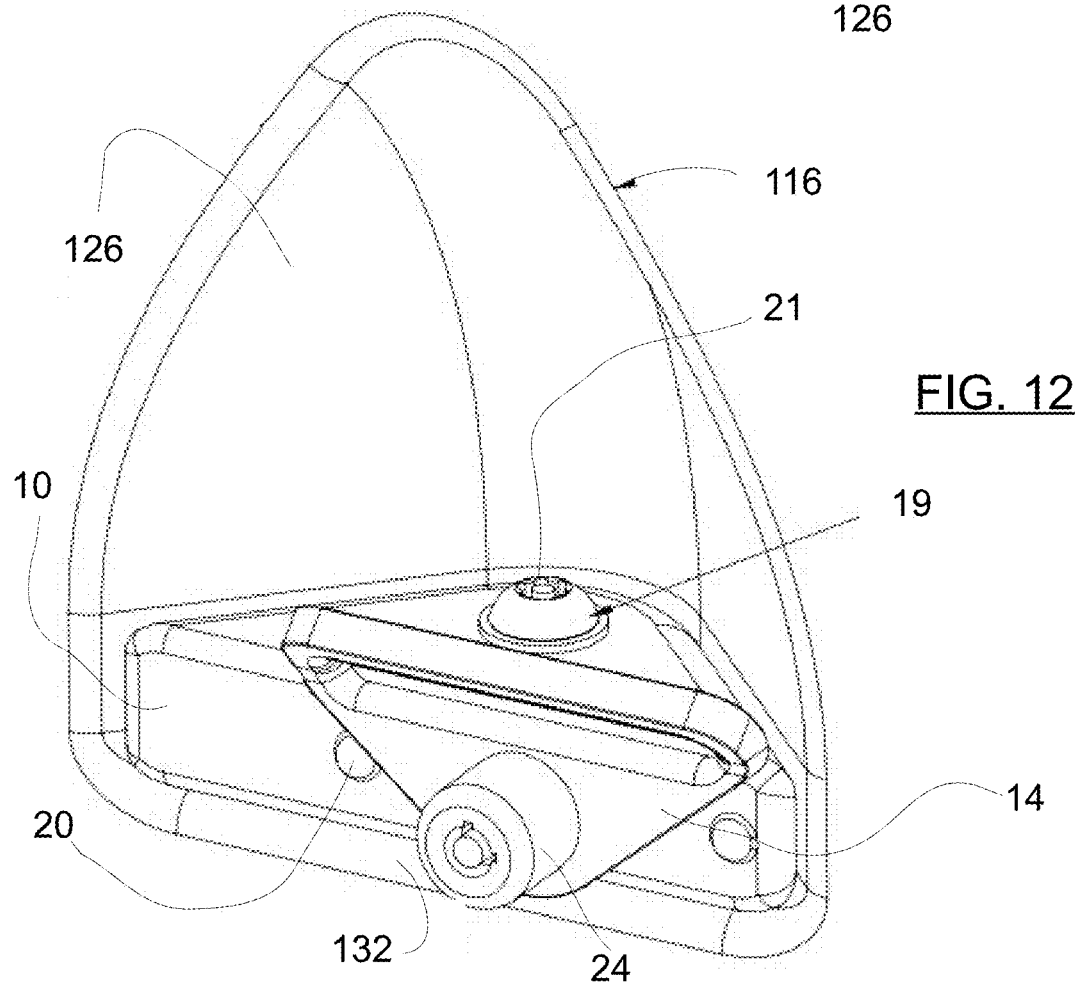
FIG. 12 is a section view of the first embodiment of the present invention of FIG. 1 attached to the bed of FIG. 11.

Referring to FIG. 11-12, bed 116 may have a side wall 118 having fastener coves 128 molded therein adjacent the bed bottom 130. Cove 128 comprises a side wall 126 and bottom wall 132. Anchor fastener 19 extends through base 10 to engage bottom wall 132 to removably attach base 10 to bed 116. Anchor fastener 19 may be a threaded fastener having a tamper resistant head 21. Anchor fastener may alternatively attach base 10 to floor or wall.

Figure 13:
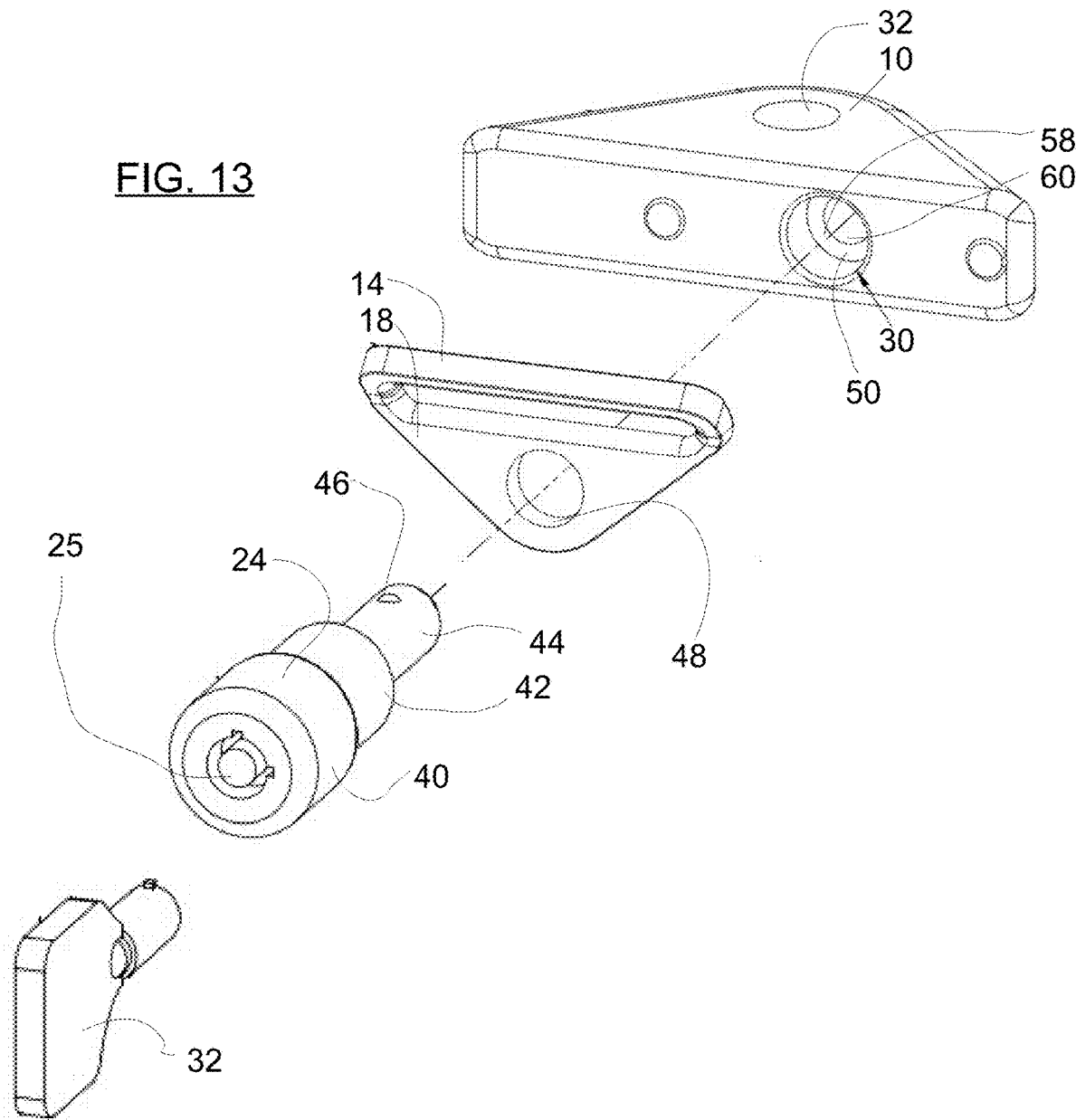
FIG. 13 is an exploded view of the first embodiment of the present invention.

Referring to FIG. 13. Quick release fastener 24, may have locking head 40 with release mechanism 25. Release mechanism 25 may be operated by actuator 32 adapted to release quick release fastener 24 from base 10. Release mechanism 25 may be a key, a magnetic actuator, a bio-metric scanner, a remote control release, a combination lock or other actuator device. Quick release fastener 24 may comprise a head 40 having a ring shaft 42 extending therefrom. A base shaft 44 may extend from ring shaft 42. Base shaft 44 may have locking mechanism 46 contained therein. Locking mechanism 46 may have retractable fixtures extending perpendicular to base shaft 44. Locking mechanism 46 may be actuated by release mechanism 25.

Continuing to refer to FIG. 13, quick release hole 30 may comprise ring opening 50 and locking shoulder 58 and shaft portion 60. Restraint ring 14 may have a restraint hole 48 extending there-through. When assembled, ring shaft 42 is adapted to extend into shaft portion. Locking mechanism 46 releasably engages locking shoulder 58. ring shaft extends through restraint hole 48 and is in ring opening 50. Release mechanism 25 actuates the locking mechanism 46 into a non-locking configuration whereby quick release fastener is extended through restraint hole 48 and into base 10 at quick release hole 30. Base shaft 44 in shaft portion 60 is adapted to hold locking mechanism adjacent locking shoulder 58. Release mechanism 25 may be disengaged to extend locking mechanism 46 adapted to bear against locking shoulder 58. Head 40 bears against ring base 18 thereby removably securing restraint ring 14 to base 10.

Figure 14:
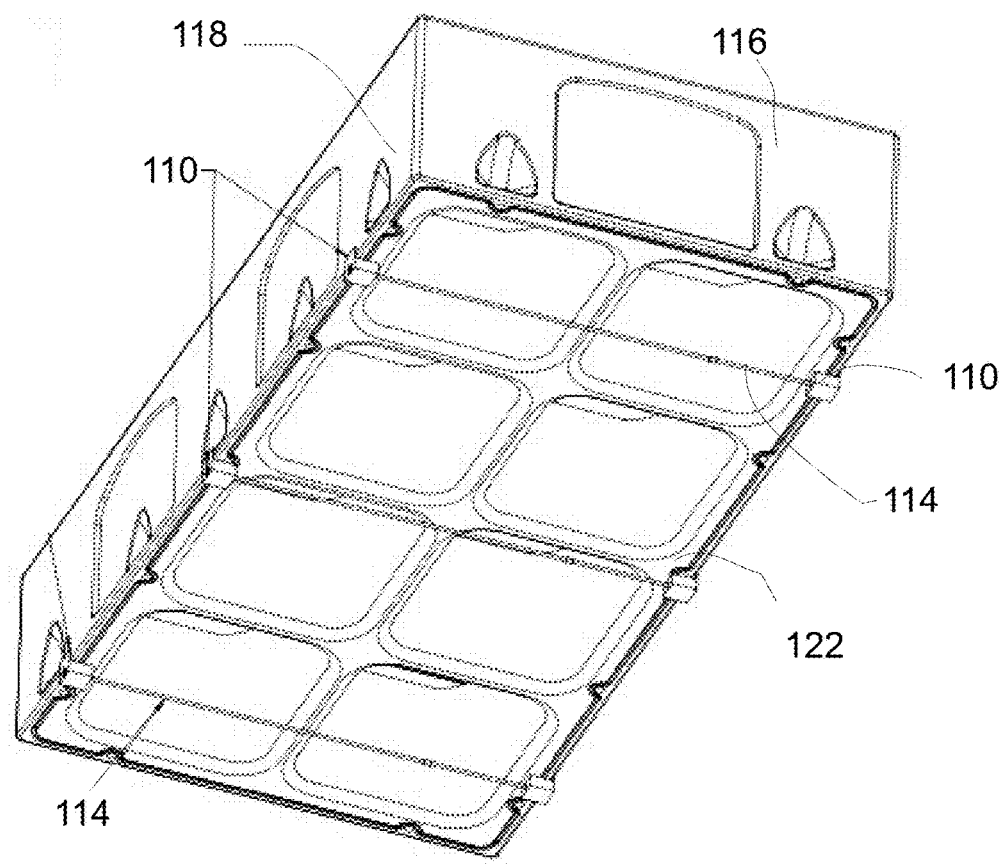
FIG. 14 is a bottom perspective view of a second embodiment of the present invention attached to a bed.
Figure 15:
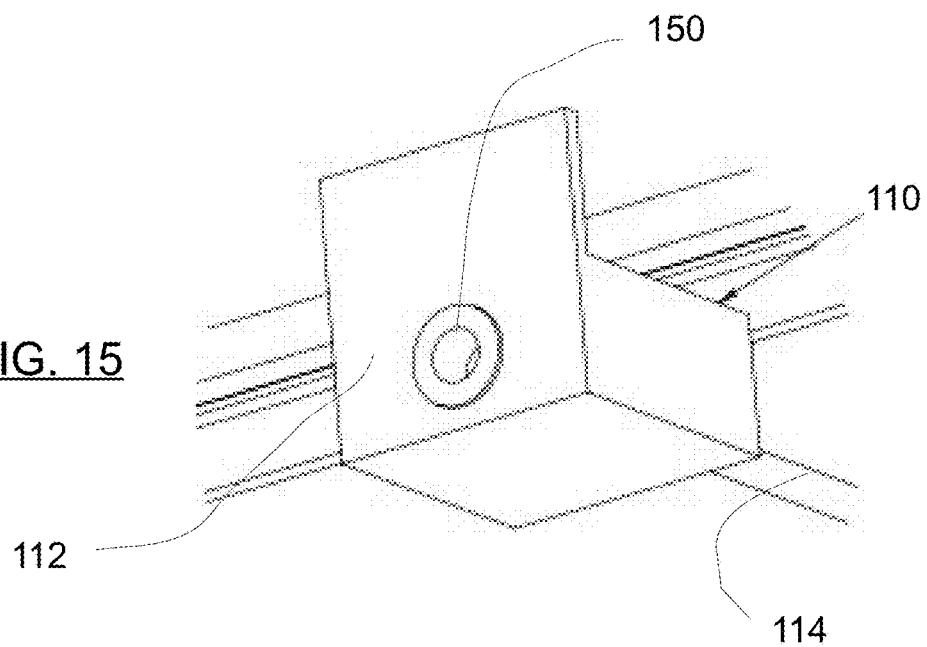
FIG. 15 is a perspective view of the second embodiment of the present invention.

Referring to FIGS. 14 and 15, base 110 may be attached rod 114 extended under bed 116. Rod 114 may be attached to first and second base 110. First and second base 110 bear against sidewalls 118 to dispose ring opening 150 adapted to receive quick release fastener 24. base 110 may have flange 112 bearing against bed 116.

Figure 16:
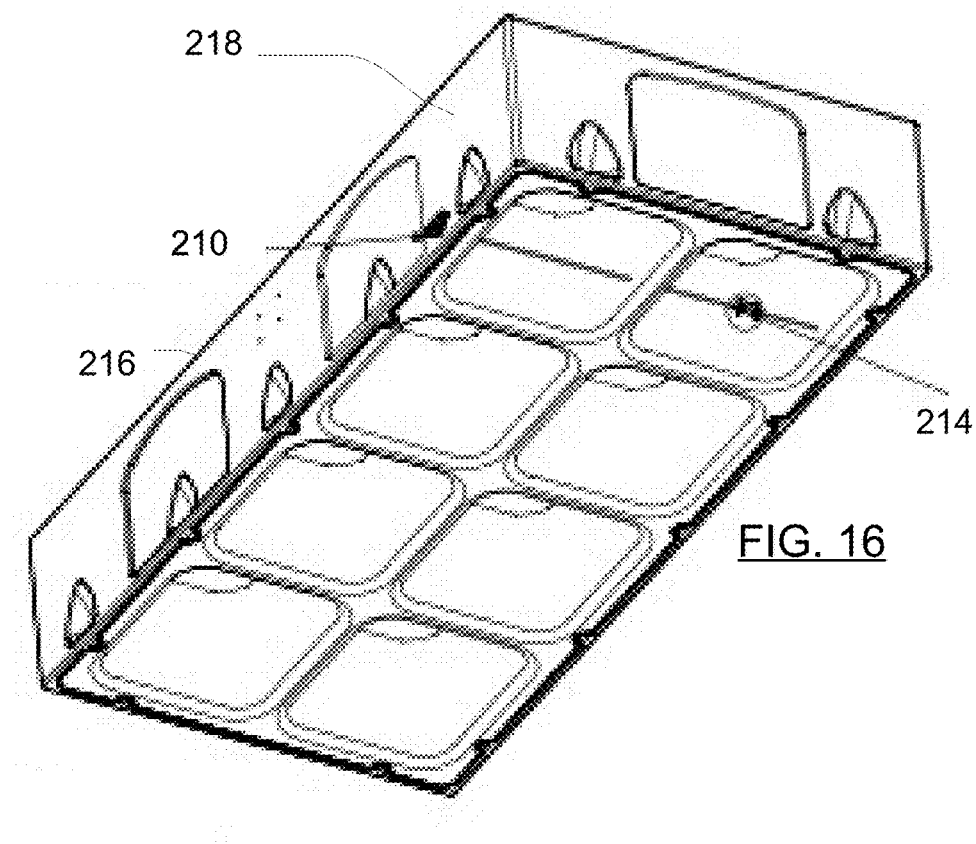
FIG. 16 is a perspective view of a third embodiment of the present invention.
Figure 17:
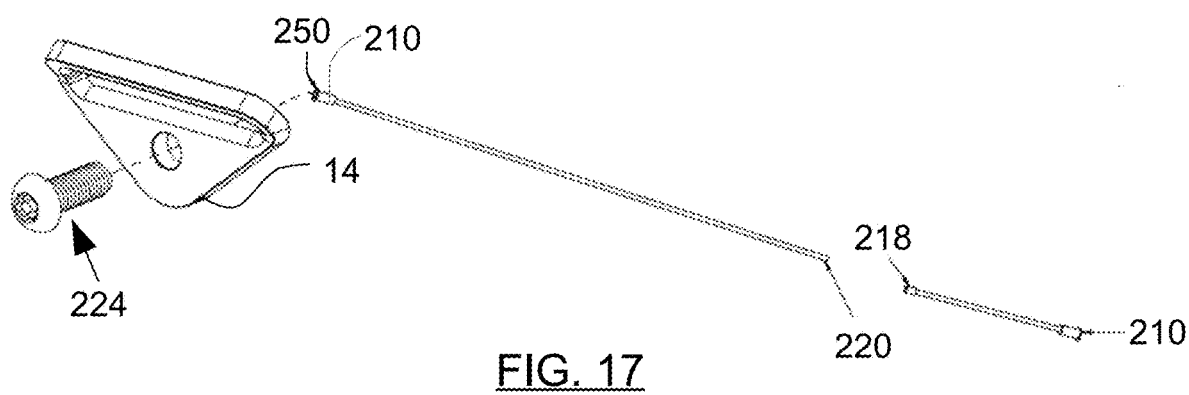
FIG. 17 is an exploded view of the third embodiment of the present invention.

Referring to FIGS. 16 and 17, base 210 may comprise ring opening 250 on the end of shaft 214. Shaft 214 may be pierced through bed 216. Ring opening 250 may be adapted to removably receive quick release fastener 224. Quick release fastener 224 may releasably connect restraint ring 14 to bed 216. Threaded coupling 218, 220 may be used to adapt shaft 214 to dispose base 210 on outside wall 218 of bed 216.

Figure 19:
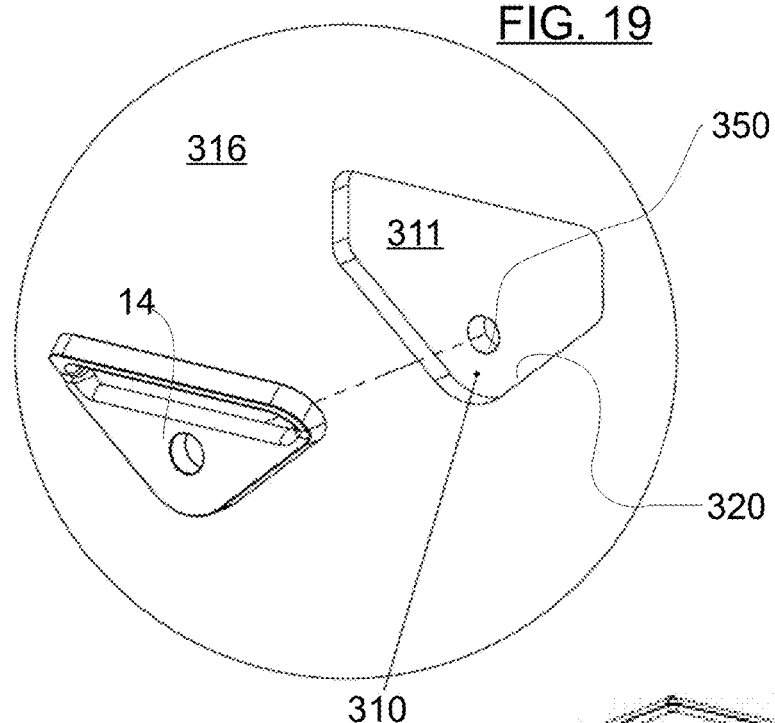
FIG. 19 is an exploded section view of the fourth embodiment of the present invention taken at approximately 19-19 of FIG. 18.
Figure 18:
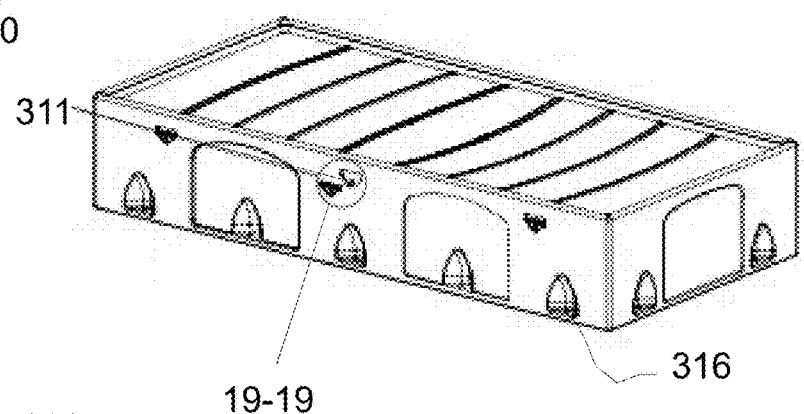
FIG. 18 is an perspective exploded view of the fourth embodiment of the present invention.
Figure 20:
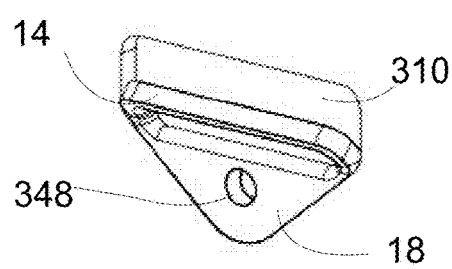
FIG. 20 is a section view of the fourth embodiment of the present invention taken at approximately 19-19 of FIG. 18

Referring to FIGS. 18-20, base 310 may comprise a pocket 311 formed on a molded bed 316. Pocket 311 may further comprise ring opening 350 and stabilizer edge 320 adapted to engage restraint ring 14 to hold restraint 314 in a predetermined orientation. Restraint hole 348 is disposed to align with ring opening 350.

Referring to FIGS. 21-23, base 410 may comprise bolt on pocket 411 attached to bed 416 on wall 418. Bolt on pocket 411 may comprise a restraint plate 417 adapted to bolt to bed 416. Restraint plate 417 may comprise ring opening 450 and stabilizer edge 420. Restraint ring 14 may fit in pocket 411 having ring opening 450 aligned with restraint hole 438. Tamper resistant quick turn fastener 456 may be adapted to removably attach restraint ring 14 to bolt on pocket 411.

Referring to FIGS. 24-26, quick release fastener 24 may be a ball lock pin 500 comprising a tamper resistant actuator 502, a body 504 and a ball tube 506, the ball tube 506 comprising a ball hole 508 having a ball 510 partially extending from the ball tube 506, the body 504 comprising a key end 512 and a ball tube end 514, the ball tube 506 on the ball tube end 514, the key end 512 having key opening 518. The body 504 having a ligature resistant taper 520 on the key end, the ball tube 506 having a body end 522 and a furniture end 524. The body 504 may further comprise a head 526. The head 526 comprising the key end 512 and a ring end 528. Key end 512 may have a first diameter designated as D1. Ring end 528 may have a second diameter designated as D2. D2 is lager than D1 thus defining the tapered outer surface 520.

Continuing to refer to FIGS. 24-26, the ball lock pin 500 may further comprise an actuator 530 extending from the key end 512. The actuator 530 attached to a locking mechanism 532, a keyed release 534 and a spring 536. Actuator 530 bears against ball shaft 538 disposed in ball tube. Ball shaft 538 has ball cam surface 540 bearing against ball 510 to urge ball 510 into ball hole 508. Tapered surface 520 may extend from key end 512 toward ring end 514. Keyed end has a diameter designated as D1.

Referring to FIGS. 27 to 33, base 10 may comprise a ring side 542 spaced from furniture 116. Locator beads 20 may be disposed on ring side 542. Pin chamber 544 may comprise opening 546 in ring side 542. Pin chamber 544 may further comprise body portion 548 and lock portion 549. Collar 550 may be disposed concentrically on body 504 between head 512 and base 10. Collar 550 may comprise tapered outer surface 552, head end 556 and open interior 554. Tapered outer surface is disposed at an angle to an axis A of collar 550 at an inward angle designated as T. T may be an acute angle. Collar head end 556 may have a diameter designated as D2. Collar may further comprise a base end 558 having a diameter designated as D3. D3 is generally larger than D2 defining the tapered outer wall 552 of collar 550. D2 may be generally equal to D1 to provide smooth transition from tapered end 512 to tapered wall 552. Base end 558 is adapted to bear against base 10. Collar 550 may be disposed on ball lock pin 500 when ring 14 is removed. It should be understood, collar 550 may be disposed on body 504 when ring 14 is removed to continue tapered head shape 520 between key end 512 and base 10. Lock portion may further comprise first ball recess being a groove in the wall of lock portion concentric with ball tube 506. Alternatively, as shown in FIG. 30, body 504 may be in body portion 546. Ball tube may be in lock portion 549 Ball 510 may protrude from ball tube 506. Ball 510 may be in first ball recess 560 formed concentrically in lock portion 549. Second ball recess 562 may be formed in lock portion 549 between first ball recess 560 and furniture end 564. Second ball recess 562 may be spaced from first ball recess 560 a distance approximately equal to or larger than the thickness of ring 14.

In summary, referring to FIGS. 1-33 the base 10, 110, 210, 310, 410 (FIGS. 1, 14, 17, 19, 22, respectively) may be configured with a pin chamber having a removable fastener for removably attaching a restraint ring to furniture 501 such as a bed or chair or the like. Base 10 is attached to furniture. A ligature resistant ball pin lock having tapered head is attached to base whereby the restraint ring is captured between the tapered head and the base. The tapered head prevents the attachment of ligatures. The restraint ring may be removed and replaced by a collar having a tapered outer surface that aligns with the tapered head to fill the space left by the restraint ring removal and provide a tapered surface from the protruding key end of the ball pin lock to the base. The ball pin lock may be released from the base by mechanical arrangement such as a key or by other means such as electrical or magnetic release.

The removable restraint ring receptacle 500 maybe kitted with a ring base, the ring base comprising a bed surface, a mounting surface and a pin chamber. The pin chamber comprising an opening in the mounting surface, a first body chamber and a first lock chamber. The opening comprising an axis, the first body chamber concentric with the axis and the first body chamber in fluid communication with the opening. The first body chamber comprising a first end, a second end and a generally cylindrical first pin wall extending from the first end to the second end. The first end on the opening. The first lock chamber concentric with the axis. The first lock chamber in communication with the first body chamber. The first lock chamber comprising a generally cylindrical first lock wall, a body end and a bed end. The lock wall extending from the pin end to the bed end. The pin end on the second end. The first lock wall may be generally concentric with the first body wall. The first lock wall further comprising a first ball recess. The first ball recess formed in the first lock wall. The first ball recess between the body end and the wall end.

The ring fastener may comprise a ball lock pin comprising a tamper resistant actuator, a body and a ball tube. The ball tube comprising tube extending from the body having a ball and a shaft therein. The ball in a locked position partially extending from the ball tube and in the first ball recess. The body in the first body chamber. The body comprising a key end and a ball tube end. The ball tube on the ball tube end. The key end having a key opening with a key therein whereby the key is adapted to move the shaft to release the ball to an unlocked position inside the ball tube. The body having a ligature resistant taper on the key end. A collar on the body, the collar extending from the key opening to the ring surface, the collar having a tapered surface sloped away from the base.

Thea ring comprising an outside, a base and a bed side, a hole in the base extending from the outside to the bed side, the body in the hole, the ring surface on the outside, the bed side on the mounting surface.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given. Further, the present invention has been shown and described with reference to the foregoing exemplary embodiments. It is to be understood, however, that other forms, details, and embodiments may be made without departing from the spirit and scope of the invention which is defined in the following claims.

We claim:

1. A ligature resistant restraint ring receptacle for attaching a restraint ring to a furniture piece, the restraint ring having a ring base comprising a pin chamber therein, the ligature resistant restraint ring receptacle comprising:

a ball pin lock, the ball pin lock comprising a ligature resistant head, a body and a lock tube, the ligature resistant head comprising a conical shape, the body on the head, the lock tube on the body, the ligature resistant head adapted to bear against the ring base, the lock tube attached to the furniture; and a collar, the collar having an outside surface, the collar having an open interior, the body in the open interior, the collar between the head and the furniture, a ligature resistant tapered outside surface on the collar, the tapered outside surface extending from the head, wherein the tapered outside surface bears on the conical shaped head.

2. The ligature resistant restraint ring receptacle of claim 1, further comprising a base, the base having a ring side and a furniture side, the base adapted to attach to the furniture, the base further comprising a pin chamber opening into the ring side and a mounting hole, the body in the pin chamber.

3. The ligature resistant restraint ring receptacle of claim 2, further comprising a stabilizer on the base, the stabilizer adapted to bear against the restraint ring base.

4. The ligature resistant restraint ring receptacle of claim 3, wherein the pin chamber further comprises a body portion and a lock portion.

5. The ligature resistant restraint ring receptacle of claim 1, further comprising a bolt on pocket adapted to receive the base, the bolt on pocket adapted to attach to the furniture.

6. A removable restraint ring receptacle for attachment of a restraint ring to furniture, the restraint ring comprising a mounting plate, the mounting plate comprising a receptacle side and pin side, a pin hole in the mounting plate, the pin hole extending from the receptacle side to the pin side, the removable restraint ring receptacle comprising:

a ring base, the ring base comprising a furniture side, a ring side and a pin chamber, a body portion and a lock portion, the opening in the ring side, the body portion comprising an open generally cylindrical body chamber extending from the opening to the lock portion, the lock portion comprising an open generally cylindrical lock chamber comprising a furniture end and a body end, the body end in fluid communication with the lock chamber, the lock chamber extending from the body portion, a first ball recess in the lock chamber, the first ball recess generally formed in a lock chamber wall, the first ball channel between the furniture side and the body portion; and a ligature resistant lock pin, the lock pin comprising a head, a body and a lock tube, the head comprising a key end, a tapered exterior head surface and a ring end, the ring end having a first diameter, the key end having a second diameter, the second diameter smaller than the first diameter, the body comprising a head end and a lock end, the head end on the ring end, the lock tube comprising a body end and a ball end, the body end on the lock end, a ball in the body end, the ball partially extending from the lock tube, the body in the body portion, the lock tube in the lock portion, the ball in the first ball channel, the head bearing against the pin side, the body in the pin hole whereby the mounting plate is between the ring side and the pin head, a tapered collar, the tapered collar comprising a generally cylindrical interior collar opening, a tapered exterior collar surface, a head end and a base end, the tapered exterior collar surface having a third diameter at the head end and a fourth diameter at the base end, the third diameter generally equal to the first diameter, the fourth diameter larger than the third diameter whereby the body is adapted to be in the interior collar opening or the pin hole.

7. The removable restraint ring receptacle of claim 6, wherein the pin chamber further comprises an axis, the opening concentric about the axis, the body portion comprising a generally cylindrical body chamber concentric about the first axis, the pin portion comprising a generally cylindrical pin chamber concentric about the first axis.

8. The removable restraint ring receptacle of claim 7, wherein the ligature resistant lock pin has a second axis, the second axis aligned with the first axis.

9. The removable restraint ring receptacle of claim 7, wherein the collar head end bears on the head, the collar receptacle end bears on the base whereby the tapered exterior head surface extends from the key end to the collar head end.

10. The removable restraint ring receptacle of claim 9, wherein the collar head end bears on the head, the collar receptacle end bears on the base.

11. The removable restraint ring receptacle of claim 6, further comprising a second ball channel in the pin chamber, the second ball channel between the first ball channel and the furniture side.

12. The removable restraint ring receptacle of claim 6, wherein the collar has a first length between the head end and the base end, the second ball recess spaced from the first ball recess by the first length.

13. The removable restraint ring receptacle of claim 12, wherein the ring end is spaced from the ring side by a second length, the first length substantially equal to the second length.

14. The ligature resistant restraint ring receptacle of claim 1, further comprising a pocket, the pocket on the furniture, the pocket comprising and a ring opening and a stabilizer.

15. The ligature resistant restraint ring receptacle of claim 14, wherein the ring base is disposed in the pocket, the ring base on the stabilizer.

* * * * *